US009719146B2

(12) United States Patent
Bhaumik et al.

(10) Patent No.: US 9,719,146 B2
(45) Date of Patent: Aug. 1, 2017

(54) COMPOSITION AND METHOD FOR IMAGING STEM CELLS

(75) Inventors: Srabani Bhaumik, Niskayuna, NY (US); Sanjiv Sam Gambhir, Portola Valley, CA (US); Ramasamy Paulmurugan, Mountain View, CA (US); Shahriar Yaghoubi, Palo Alto, CA (US); Byeong-Cheol Ahn, Daegu (KR); Natesh Parashurama, San Mateo, CA (US)

(73) Assignee: General Electric Company, Niskayuna, NY (US)

( * ) Notice: Subject to any disclaimer, the term of this patent is extended or adjusted under 35 U.S.C. 154(b) by 44 days.

(21) Appl. No.: 12/555,901

(22) Filed: Sep. 9, 2009

(65) Prior Publication Data

US 2011/0059439 A1  Mar. 10, 2011

(51) Int. Cl.
*C12N 15/85* (2006.01)
*C12Q 1/68* (2006.01)
*C12N 15/10* (2006.01)

(52) U.S. Cl.
CPC ....... *C12Q 1/6897* (2013.01); *C12N 15/1086* (2013.01); *C12N 15/85* (2013.01); *C12N 2830/008* (2013.01); *C12N 2830/20* (2013.01); *C12N 2840/20* (2013.01)

(58) Field of Classification Search
None
See application file for complete search history.

(56) References Cited

U.S. PATENT DOCUMENTS

| | | | |
|---|---|---|---|
| 6,033,856 A * | 3/2000 | Koerner et al. | 435/6.13 |
| 6,482,937 B1 | 11/2002 | Baetscher et al. | |
| 6,818,757 B2 | 11/2004 | Lee et al. | |
| 7,008,776 B1 * | 3/2006 | Jaye et al. | 435/7.4 |
| 7,399,851 B2 | 7/2008 | Livingston et al. | |
| 7,524,674 B2 | 4/2009 | Gambhir et al. | |
| 2005/0048488 A1 | 3/2005 | Rothstein | |
| 2005/0101017 A1 * | 5/2005 | Auerbach et al. | 435/455 |
| 2005/0209231 A1 | 9/2005 | Wu et al. | |
| 2006/0110830 A1 | 5/2006 | Dominko et al. | |
| 2008/0216185 A1 * | 9/2008 | Chesnut et al. | 800/21 |
| 2008/0280362 A1 | 11/2008 | Jaenisch et al. | |
| 2009/0004740 A1 | 1/2009 | Mitalipov et al. | |
| 2009/0047263 A1 | 2/2009 | Yamanaka et al. | |
| 2009/0137023 A1 | 5/2009 | Casutt | |

FOREIGN PATENT DOCUMENTS

| | | |
|---|---|---|
| KR | 20090055869 A | 6/2009 |
| WO | 2004094642 A2 | 11/2004 |
| WO | 2007140617 A1 | 12/2007 |
| WO | 2008089396 A1 | 7/2008 |
| WO | 2008144052 A2 | 11/2008 |

OTHER PUBLICATIONS

Adler et al (Toxicology in Vitro, 2008, vol. 22, pp. 200-211).*
Murphy et al (Biochem. J. 1997. vol. 322, pp. 393-401).*
Qin et al (Biologicals, 2009, pp. 235-244).*
Rich Deem; "Induced Pluripotent Stem Cells (iPS) from Human Skin: Probable Replacement for Embryonic Stem Cells"; 3Pages.
Huiqun Yin, Heng Wang, Hongguo Cao, Yunhai Zhang, Yong Tao and Xiaorong Zhang; "Cell reprogramming for the creation of patient-specific pluripotent stem cells by defined factors"; Journal Frontiers of Agriculture in China, Publisher Higher Education Press, co-published with Springer-Verlag GmbH ISSN 1673-7334 (Print) 1673-744X (Online) Issue vol. 3, No. 2/Jun. 2009, Category Review DOI 10.1007/s11703-009-0028-8; 3 Pages.
Kazutoshi Takahashi, Koji Tanabe, Mari Ohnuki, Megumi Narita, Tomoko Ichisaka,Kiichiro Tomoda and Shinya Yamanaka; "Induction of Pluripotent Stem Cells from Adult Human Fibroblasts by Defined Factors"; Takahashi et al., Induction of Pluripotent Stem Cells from Adult Human Fibroblasts by Defined Factors, Cell (2007), doi:10.1016/j.cell.2007.11.019; 12Pages.
Hu Wang, Feng Cao, Abhijit De, Yuan Cao, Christopher Contag, Sanjiv S. Gambhir, Joseph C. Wu and Xaoyuan Chen ; "Trafficking Mesenchymal Stem Cell Engraftment and Differentiation in Tumor-Bearing Mice by Bioluminescence Imaging"; Department of Radiology, Bio-X Program, Stanford University School of Medicine, Stanford, California, USA; e-mail: shawchen@stanford.edu; accepted for publication Mar. 24, 2009; first published. online in Stem Cells Express Apr. 2, 2009. VC AlphaMed Press 1066-5099/ 2009/$30.00/0.
Rebecca Stewart, Chunbo Yang, George Anyfantis, Stefan Przyborski, Nicholas Hole, Tom Strachan, Miodrag Stojkovic, W Nicol Keith, Lyle Armstrong and Majlinda Lako ; "Silencing of the expression of pluripotent driven-reporter genes stably transfected into human pluripotent cells"; © future Medicine Ltd ISSN 1746-0751; 18Pages.

(Continued)

*Primary Examiner* — Celine Qian
(74) *Attorney, Agent, or Firm* — Pabitra K. Chakrabarti

(57) ABSTRACT

An expression vector, comprising a first reporter nucleic acid sequence operably linked to a first expression control sequence comprising a promoter; and a second reporter nucleic acid sequence operably linked to a second expression control sequence that comprises a response element that is activated or inactivated as one or more of the cells differentiate or dedifferentiate. Methods and kits for imaging and monitoring stem cells comprising the expression vector are also provided.

4 Claims, 10 Drawing Sheets

(56) References Cited

OTHER PUBLICATIONS

Jeong Tae Do and Hans R. Scholer; "Regulatory circuits underlying pluripotency and reprogramming"; 0165-6147/$—see front matter 2009 Elsevier Ltd. All rights reserved. doi:10.1016/j.tips.2009.03.003 Available online May 6, 2009; 7Pages.

Duanqing Pei; "Regulation of Pluripotency and Reprogramming by Transcription Factors"; Published, JBC Papers in Press, Sep. 26, 2008, DOI 10.1074/jbc.R800063200; The Journal of Biological Chemistry vol. 284, No. 6, pp. 3365-3369, Feb. 6, 2009; © 2009 by The American Society for Biochemistry and Molecular Biology, Inc. Printed in the U.S.A.

William E Lowry and Kathrin Plath; "The many ways to make an iPS cell"; vol. 26, No. 11 Nov. 2008 nature biotechnology; 3Pages.

Saskia L. M. A. Beeres, MD, Frank M. Bengel, MD, Jozef Bartunek, MD Douwe E. Atsma, MD, Jonathan M. Hill, MD, Marc Vanderheyden, MD, Martin Penicka, MD, Martin J. Schalij, MD, William Wijns, MD and Jeroen J. Bax, MD; "Role of Imaging in Cardiac Stem Cell Therapy"; Journal of the American College of Cardiology vol. 49, No. 11, 2007; © 2007 by the American College of Cardiology Foundation ISSN 0735-1097/07/$32.00; Published by Elsevier Inc.; 12Pages.

PCT/EP2010/063054 Search Report, Jan. 31, 2011.

J. Tian et al., "Independent and high-level dual-gene expression in adult stem-progenitor cells from a single lentiviral vector" Gene Therapy, vol. 16, No. 7, Jul. 2009, pp. 874-884.

Y. Xiaobing et al., "Lentiviral Vectors with Two Independent Internal Promoters Transfer High-Level Expression of Multiple Transgenes to Human Hematopoietic Stem-Progenitor Cells," The Journal of the American Society of Gene Therapy, vol. 7, No. 6, Jun. 2003. pp. 827-838.

P. Guangjin et al., "A negative feedback loop of transcription factors that controls stem cell pluripotency and self-renewal," The FASEB Journal: Official Publication of the Federation of American Societies for Experimental Biology, vol. 20, No. 10, Aug. 2006, pp. 1730-1732.

Written Opinion issued in connection with corresponding SG Application No. 201201639-0 dated Jul. 18, 2013.

Unofficial English translation of JP Office Action issued in connection with corresponding JP Application No. 2012-528336 on Aug. 26, 2014.

\* cited by examiner

SEQUENCE LISTING

```
<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcggatccgc caccatggaa gacgccaa                                            28

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcggtaccct acttgtacag ctcgtccatg ccg                                      33

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggatcgat aacccgtgtc ggctccagat                                          30

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcgtcttcc atggatcctc                                                     20

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ctcgagttga agataaagct acggataacg ctgcttgaag ataaagctac ggataacgc          59
```

```
<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgccgggggg ctataaaagg gggtgggggc gttcgtcctc actctaagct t          51
```

COMPOSITION AND METHOD FOR IMAGING STEM CELLS

SEQUENCE LISTING

The instant application contains a Sequence Listing which has been submitted via EFS-Web and is hereby incorporated by reference in its entirety. Said ASCII copy, created on Nov. 18, 2009, is named 238569.1.txt, and is 1,735 bytes in size.

FIELD

This invention relates generally to imaging cells, and more particularly to imaging expressed reporter nucleic acid sequences using novel expression vectors in stem cells.

BACKGROUND

Non-invasive and repetitive imaging of a single cell or groups of cells in a living subject is crucial for in vivo tracking of cells, particularly in the field of cell-based therapy. Different imaging modalities have been used for understanding normal physiology and disease progression in many applications including cell-based therapies, cell trafficking, or gene therapy studies. Expression vectors having reporter nucleic acid sequences offer possibilities for non-invasive quantitative imaging of gene expression in living subjects.

To unravel the complexity and dynamics of molecular and cellular events, it is desirable to image the reporter gene expression in individual cells with the help of a single or multiple reporter gene construct. An imaging reporter gene encodes a protein that is detectable by various non-invasive imaging techniques. Reporter gene expression may be imaged in living subjects using optical imaging, positron emission tomography (PET), single-photon emission computed tomography (SPECT), or magnetic resonance imaging (MRI) depending on the type of reporter gene.

Stem cell-based therapy has revealed considerable potential, especially in the field of regenerative medicine. One of the obstacles for stem cell-based therapy is the lack of efficient monitoring methods to track the employed stem cells. Monitoring the differentiation status of a stem cell is essential to determining therapeutic efficacy as well as potential for adverse effects such as tumorogenicity of the implanted stem cell. Endogenous gene expression in cell culture or in living subjects may be assessed by using transgenes containing endogenous promoter driven reporter gene. Assessment of pluripotency of implanted stem cells may enable prediction of future terratoma formation. Pluripotency marker related promoter driven reporter gene system may help detect the differentiation status of a stem cell.

To overcome the shortcomings of each modality, a multimodality approach may be useful, which detect a plurality of different reporter gene expression. Moreover, a robust method to monitor the stem cell activity using non-invasive reporter gene imaging technique in living animal is a highly desirable goal.

BRIEF DESCRIPTION

The invention generally comprises an expression vector comprising one or more reporter sequence(s). The invention further comprises methods and kits for monitoring cellular activity by imaging reporter nucleic acid expression.

An example of an expression vector for monitoring stem cells comprises a first reporter nucleic acid sequence operably linked to a first expression control sequence and a second reporter nucleic acid sequence operably linked to a second expression control sequence. The first expression control sequence comprises a promoter. The second expression control sequence comprises a response element that activates or inactivates in response to one or more stages of cell differentiation or dedifferentiation.

An example of an expression vector comprises a first reporter nucleic acid sequence operably linked to a first expression control sequence; and a second reporter nucleic acid sequence operably linked to a second expression control sequence. The first expression control sequence comprises a promoter for one or more pluripotency markers. The second expression control sequence comprises a response element that is responsive to binding of one or more response element specific proteins.

An example of a method for monitoring a stem cell comprises delivering a first expression vector comprising a first reporter nucleic acid sequence and a second reporter nucleic acid sequence to the stem cell; and monitoring the stem cell by imaging at least one of the first or second reporter nucleic acid sequence expression. The first reporter nucleic acid sequence is operably linked to a first expression control sequence comprising a promoter for one or more pluripotency markers. The second reporter nucleic acid sequence is operably linked to a second expression control sequence comprising a response element that is responsive to binding of one or more response element specific proteins, or a cell specific promoter that is regulated by one or more cell specific proteins.

An example of a kit for monitoring stem cells comprises an expression vector, wherein the expression vector comprises a first reporter nucleic acid sequence operably linked to a first expression control sequence; and a second reporter nucleic acid sequence operably linked to a second expression control sequence. The first expression control sequence comprises an Oct4 promoter, and the second expression control sequence comprises a response element that is responsive to the binding of a GATA4 protein.

An example of an expression vector comprises a first reporter nucleic acid sequence operably linked to a first expression control sequence comprising a promoter for one or more pluripotency markers; and a second reporter nucleic acid sequence operably linked to a second expression control sequence comprising a cell specific promoter that is regulated by one or more cell specific proteins.

DRAWINGS

These and other features, aspects, and advantages of the present invention will become better understood when the following detailed description is read with reference to the accompanying drawings in which like characters represent like parts throughout the drawings, wherein:

FIG. 1 is a schematic drawing of an embodiment of a construct of the invention with constitutive Ubiquitin promoter, and a cell specific Oct4 promoter.

FIGS. 2A-D are graphs showing the specificity of Oct4 expression in embryonic stem cells or in differentiated adult cell lines.

FIG. 3 is a graph of renilla luciferase expression in mouse ES cells transiently transfected with Oct4-hRLuc.

FIGS. 4A-B are graphs of luciferase expression of mouse ES cells that stably expresses Oct4-hRLuc and Ubiq-FLuc-eGFP.

FIG. 7 discloses SEQ ID NOS 5 and 6, respectively, in order of appearance.

Figure 11:
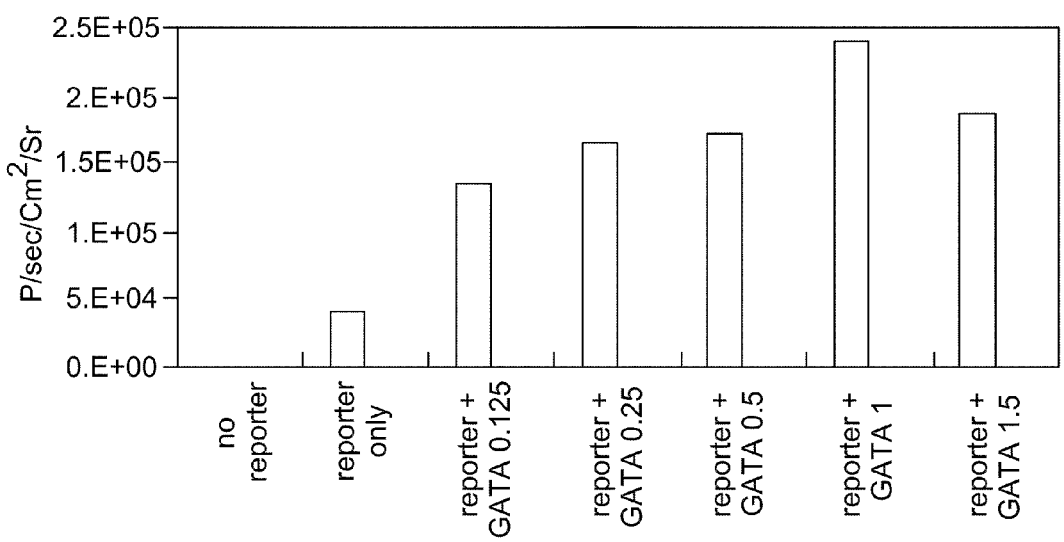

FIG. 11 a bar graph of luciferase expression of a reporter nucleic acid sequence operably linked to a response element that is responsive to GATA4 binding, in HEK 293 cells.

Figure 12:
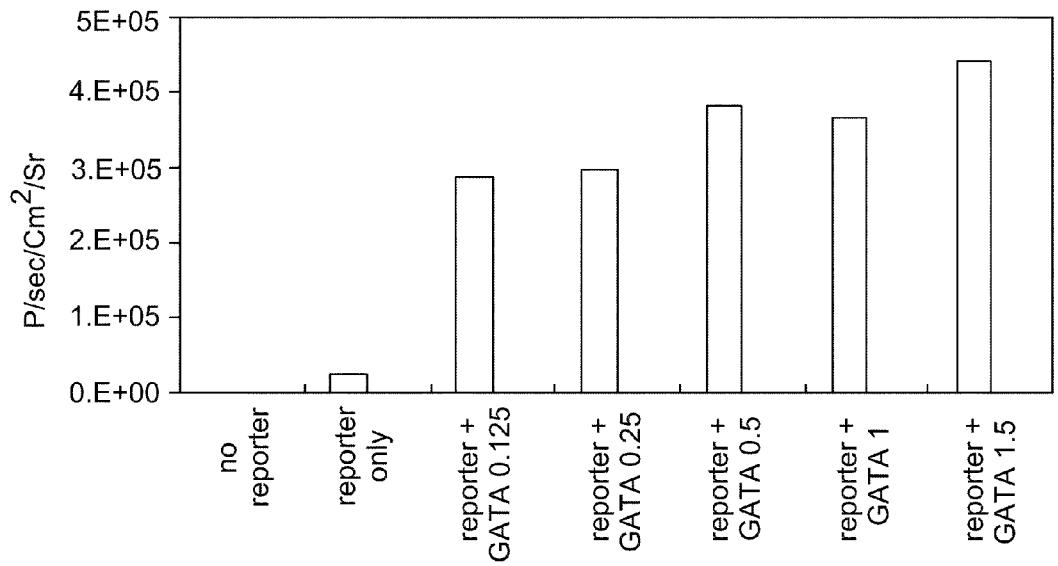

FIG. 12 is a bar graph of luciferase expression of a reporter nucleic acid sequence operably linked to a response element that is responsive to GATA4 binding, in HCT 116 colon cancer cells.

Figure 13:
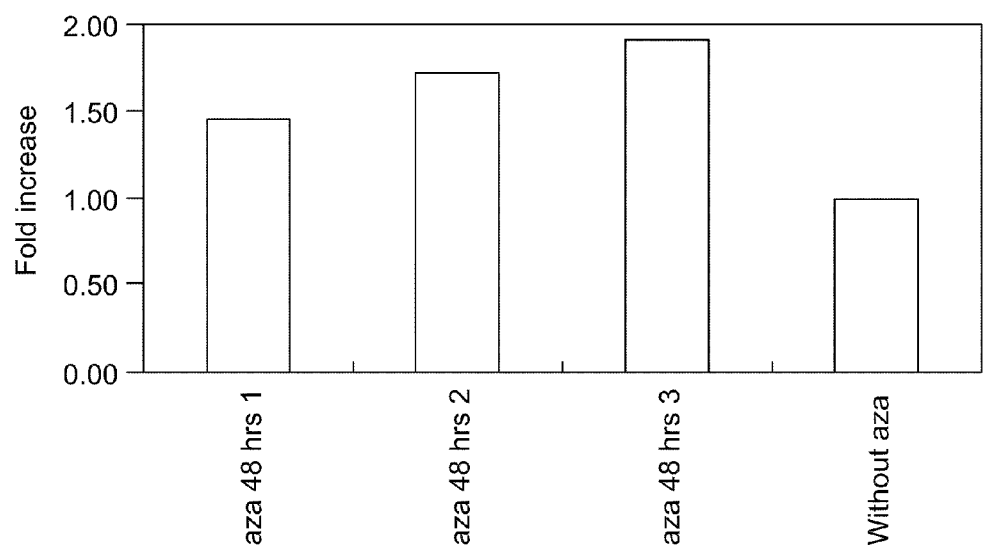

FIG. 13 is a bar graph of luciferase expression of a reporter nucleic acid sequence operably linked to a response element that is responsive to GATA4 binding, after treating HCT 116 colon cancer cells with 5-azacytidine.

Figure 14:
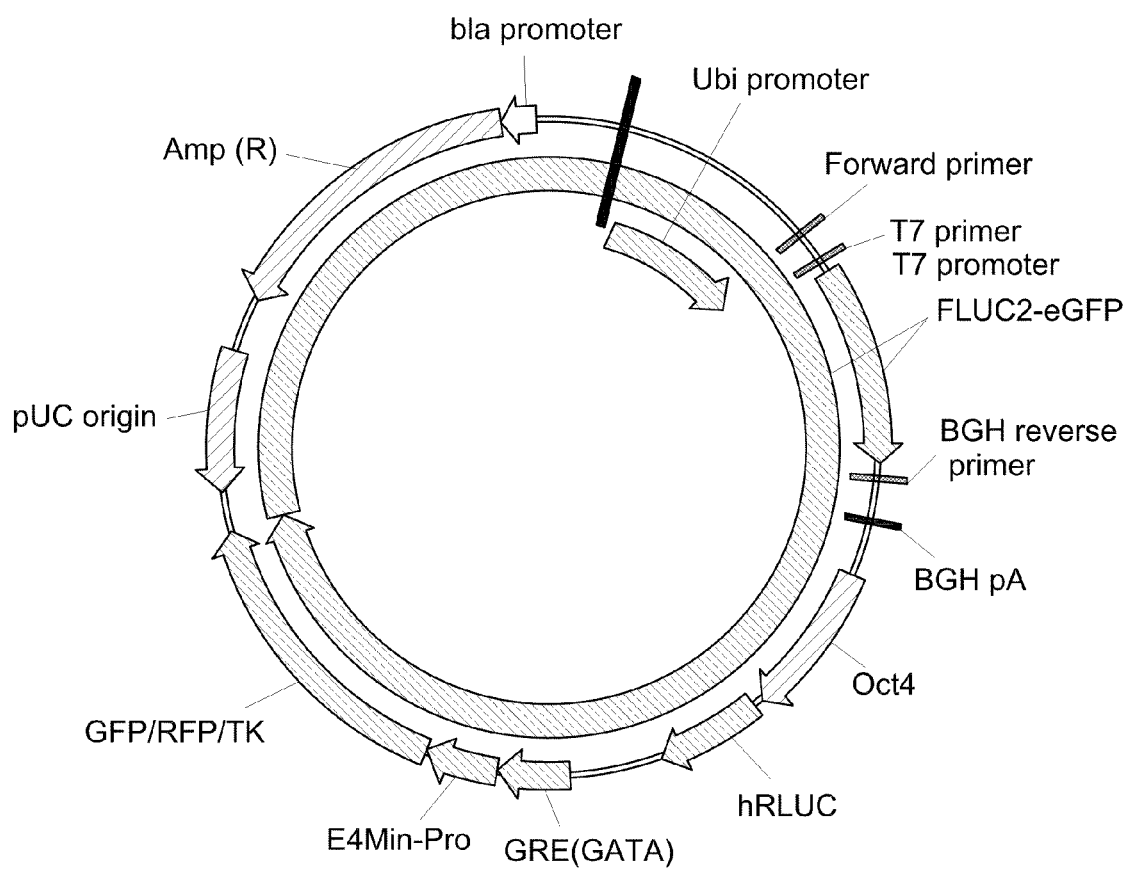

FIG. 14 is a schematic drawing of an embodiment of a construct of the invention comprising a constitutive promoter (Ubiquitin), a cell specific promoter (Oct4), and a response element (responsive to GATA4).

DETAILED DESCRIPTION

To more clearly and concisely describe and point out the subject matter of the claimed invention, the following definitions are provided for specific terms, which are used in the following description and the appended claims. Throughout the specification, exemplification of specific terms should be considered as non-limiting examples.

The term "expression vector" or "expression construct" as used herein, refers to a plasmid that may be used to introduce a specific gene or a specific nucleic acid sequence or an expression sequence tag into a target cell. Once the expression vector is inside the cell, the protein that is encoded by the nucleic acid sequence may be produced by the cellular transcription and translation machinery. The expression vector may comprise a regulatory nucleic acid sequence or an expression control sequence, a transcription initiation sequence, a nucleic acid sequence of interest (e.g., a reporter nucleic acid sequence), a transcription termination sequence or a combination thereof. The expression control sequence may comprise sequences that act as an enhancer and/or a promoter for efficient transcription of the nucleic acid sequence or the expression sequence tag that encodes the protein of interest.

The term "reporter nucleic acid sequence" or "reporter gene" as used herein, refers to a nucleic acid sequence that encodes a protein or a peptide having reporter activity. The reporter nucleic acid sequence may encode a protein or peptide that may be independently detected. A commonly used reporter nucleic acid sequence encodes a protein or a peptide that inherently possess a visually identifiable characteristic (e.g., fluorescent protein, such as GFP) or that can generate a visually identifiable characteristic (e.g., bioluminescent protein, such as luciferase). The reporter nucleic acid sequence may be selected in such a way that it is not natively expressed in the cell or organism under study, since the expression of the reporter nucleic acid sequence is being used as a marker. Non-limiting examples of the reporter nucleic acid sequence include, nucleic acid sequence that encodes a green fluorescent protein (GFP), a red fluorescent protein (RFP), a luciferase, β-lactamase and a β-galactosidase.

The term "operably linked" as used herein, means that when two sequences of a nucleic acid molecule are linked to each other in a manner which either permits both sequences to be transcribed onto the same RNA transcript, or permits an RNA transcript, begun in one sequence, to be extended into the second sequence. Thus, two sequences, such as a promoter sequence (first sequence) and any other second sequence of DNA are operably linked if transcription commencing in the promoter sequence will produce an RNA transcript of the operably linked second sequence. For example, a reporter nucleic acid sequence encoding a reporter protein and an expression control sequence may be operably linked in such a way as to permit expression of the reporter nucleic acid sequence by activation of promoter or enhancer present in expression control sequence. To be "operably linked" it is not necessary that two sequences be immediately adjacent to one another.

The term "expression control sequence" as used herein, refers to a nucleic acid sequence that is situated upstream of the reporter nucleic acid sequence. These expression control sequence define, inter alia, the location at which the RNA polymerase binds, specifically to the promoter sequence to initiate transcription. The expression control sequence may comprise a promoter, an enhancer, a gene responsive element or a nucleic acid responsive element, or a transcription initiation sequence. The expression control sequences may be engineered to improve the efficiency of transcription and/or translation of a downstream reporter nucleic acid sequence.

The term "response element" as used herein, refers to a nucleic acid sequence, which when positioned proximate to a promoter or within the promoter is capable of regulating the transcription activity. For example, a GATA4 protein-binding sequence may be used as a response element, which is positioned proximal to a minimal promoter. The binding of a GATA4 protein may regulate the promoter activity of the minimal promoter. Non-limiting examples of response elements include a hormone response element, a cAMP response element, and a GATA4 protein-binding nucleic acid sequence.

The term "constitutive promoter" as used herein, refers to an unregulated promoter that allows continual transcription of its cognate gene. A constitutive promoter directs the expression of a gene in various parts of a living subject, continuously throughout its development. Non-limiting examples of constitutive promoters include ubiquitin promoter, CT2 promoter (encodes for ATP sulfurase), and the promoters associated with the CaMV 35S transcript or Agrobacterium Ti plasmid nopaline synthase gene.

The term "monitoring" as used herein, refers to observing or recording activities in vitro or in vivo. For example, it may be a process of routinely gathering information on progression or development of a biological process in cells, tissues, or organs. Monitoring specific activities in cells, tissues, or organs may be accomplished, for example, by imaging an imagable protein or a peptide produced in the cells or incorporated into the cells. For example, the imagable proteins or peptides may be bioluminescent or fluorescent. Monitoring may be performed, for example, to identify the presence, absence, concentration, localization, or differentiation status of the cells or the tissues. Non-limiting examples of the techniques by which imagable protein or peptide can be monitored comprise optical imaging (fluorescent and bioluminescent), PET, MRI, or SPECT.

The term "differentiation" as used herein, refers to a process by which a less specialized cell becomes a more specialized cell type. Differentiation occurs numerous times during the development of a multicellular organism as the organism changes from a single zygote to a complex system of tissues and cell types. Adult stem cells divide and create fully differentiated daughter cells during tissue repair and during normal cell turnover. Differentiation dramatically changes a cell's size, shape, membrane potential, metabolic activity, and responsiveness to signals. These changes are largely due to highly controlled modifications in gene expression. For example, a cell that is able to differentiate into many cell types is known as pluripotent cell.

The term "dedifferentiation" as used herein, refers to a cellular process where a partially or terminally differentiated cell reverts to an earlier developmental stage, usually as part of a regenerative process. Non-limiting example includes induced pluripotent stem cells (iPS). The dedifferentiated cells are able to redifferentiate into specialized cell types. For example, a specialized cell type, such as adipocyte cells may be dedifferentiated into pluripotent stem cells.

The term "pluripotency marker" as used herein, refers to pluripotent cell specific marker protein. As used herein, "pluripotent cells" refer to a population of cells that can differentiate into all three germ layers (e.g., endoderm, mesoderm and ectoderm). Pluripotent cells express a variety of pluripotent cell-specific markers. The markers have some typical cell morphology of undifferentiated cells such as, compact colony, high nucleus to cytoplasm ratio, or prominent nucleolus. The pluripotency markers are activated only when the cells are in undifferentiated pluripotent state or in dedifferentiated pluripotent state. Non-limiting examples of pluripotency markers include Oct4, Sox2, Klf4, and Nanog.

One or more embodiments of the expression vector of the invention, comprises a first reporter nucleic acid sequence operably linked to a first expression control sequence, and a second reporter nucleic acid sequence operably linked to a second expression control sequence. The first expression control sequence may comprise a promoter. In one embodiment, the first expression control sequence may comprise a promoter for one or more pluripotency markers, for one example, an Oct4 promoter. The second expression control sequence may comprise a response element that is responsive to the binding of one or more response element specific proteins, for one example, GATA4 protein. The expression vector may further comprise a third reporter nucleic acid sequence operably linked to a third expression control sequence. The third expression control sequence may comprise a constitutive promoter. In one embodiment, the constitutive promoter is a ubiquitin promoter. In the expression vector, the first, second or third reporter nucleic acid sequences may be operably linked, in frame, to the first, second or third expression control sequence respectively. In some embodiments, the expression control sequence may comprise any promoter that is activated or inactivated or any response element that is responsive to binding of any protein as cells are differentiated or dedifferentiated. Such control sequences may comprise, but are not limited to, Oct4 promoter or response element responsive to GATA-4 protein binding.

In expression vectors, the first, second or third expression control sequences regulate transcription of the first, second or third reporter nucleic acid sequences, or to modify the translation of the said reporter nucleic acid encoded proteins. The distance between the expression control sequence and the reporter nucleic acid sequence may be engineered for efficient transcription of the reporter proteins. The expression vector may further comprise one or more sequence(s) that may be used to tag (e.g., a fluorescent protein tag) the reporter protein in vivo or in vitro or in living system.

Expression vectors may be used for a constitutive (consistent expression) or cell specific (expression only under certain type of cell lineages) expression of the reporter nucleic acid sequences. For example, a ubiquitin promoter has constitutive expression in any viable cell. An expression vector comprising a ubiquitin promoter operably linked to a reporter nucleic acid sequence may be used for the continuous expression of the reporter nucleic acid sequence. The reporter nucleic acid sequence operably linked to a constitutive promoter (e.g., ubiquitin) can be used for imaging cell survival and proliferation. Cell specific expression may be obtained by employing promoters that respond to specific cell type. The cell specific promoter may be a promoter specific for pluripotent cells, called pluripotency marker specific promoter. For example, an Oct4 promoter as used in the expression vector of the invention is activated when the expression vector is present in a stem cell.

The second expression control sequence may further comprise a minimal promoter. The minimal promoter is a basal minimum nucleic acid sequence that is required for binding of the transcription factors and subsequent transcription of the gene operably linked to the promoter. The minimal promoter may be operably linked to a response element. The minimal promoter may be activated by the response element. Response element is responsive to binding of one or more response elements specific protein in a specific cell lineage. For example, the response element may be responsive to the binding of a GATA4 protein. The minimal promoter may be induced by the binding of the GATA4 protein to the response element. The expression of GATA4 protein increases in cardiomyocytes. Therefore, the minimal promoter, operably linked to the response element for GATA4, is induced only when the cell is undergoing differentiation to cardiac specific cell lineages, such as cardiomyocytes. In one embodiment, the minimal promoter may be selected from CMV promoter, adenovirus early promoter, adenovirus late promoter, or TATA Box promoter. In a specific embodiment, the minimal promoter is a CMV promoter.

In one embodiment, the first expression control sequence comprises an Oct4 cell specific promoter, and the second expression control sequence comprises a minimal promoter (e.g., CMV minimal promoter) operably linked to a response element, which is responsive to the binding of a GATA4 protein. The expression control sequence may regulate the expression of a nucleic acid sequence during the growth of the organisms. Some regulatable expression control sequence may be switched off during the growth of the host cells and then may be switched on again at a desired point of time to favor the expression of a large amount of a desired protein.

The first reporter nucleic acid sequence operably linked to the promoter for pluripotency marker that is expressed when the cell is a pluripotent stem cell or an induced pluripotent stem cell. For example, Oct4 promoter activity increases when the cell is in a pluripotent stage and decreases upon cellular differentiation to specific cell lineages. Therefore, the expression of the reporter gene is down regulated in cellular differentiation state. Therefore, the signal associated with the imaging reporter nucleic acid sequence operably linked to the Oct4 promoter is "on" while the cell is in pluripotent state and said signal is "off" while the cell gets differentiated.

The second reporter nucleic acid sequence operably linked to the response element and the response element is operably linked to the minimal promoter. The minimal promoter may be activated by binding of a response element specific protein, for example, GATA4 protein to the response element. In some embodiments, the response element comprises at least four repeats of GATA4 binding sequence. The expression of GATA4 protein increases while the stem cells are differentiated to cardiac specific cells, such as cardiomyocytes. Therefore, the signal associated with reporter nucleic acid sequence linked to GATA4 is "on" while the cells are in the differentiation state (to cardiac specific cells) and the said signal is "off" while the cells are pluripotent or in a dedifferentiated state. For example, when the stem cells are differentiated into cardiac specific cell lineages the expression of GATA4 protein increases. However, the expression of GATA4 protein decreases when the cardiac specific cells are dedifferentiated into induced pluripotent stem (iPS) cells.

In some embodiments, the second reporter nucleic acid sequence operably linked to the minimal promoter may be activated by binding of a cell specific protein to the response element. For one example, when the stem cell is differentiated into an endothelial cell, Fetal liver kinase-1 (FLK-1) may get activated, may bind to a response element present in the second expression control sequence and activate the minimal promoter associated with the response element. Non-limiting examples of cell specific markers are listed in Table 1. In some embodiments the second expression control sequence may comprise a differentiated cell-specific promoter. The differentiated cell specific promoters include, but not limited to the FLK-1, BM88, or HLA-Dra. In some embodiments, the cell specific markers (non limiting examples listed in Table 1) may be response element specific proteins that binsd to response lement, or cell specific proteins that bind to promoter in the differentiated cells.

TABLE 1

Cell specific markers.

| Cell Type | Marker Name |
| --- | --- |
| Endothelial | Fetal liver kinase-1 (FLK-1) |
| Smooth Muscle cell (SMC) | SMC specific myosin heavy chain, vascular endothelial cell cadherin |
| Osteoblast | Bone specific alkaline phosphatase, hydroxyapetite, osteocalcin, SPP1 |
| Mesenchymal stem cell (MSC) and progenitor cells | Bone morphogenic protein receptor (BMPR) |
| White Blood cells | CD4, CD8, leukocyte common antigen-CD45 |
| Hematopoetic stem cells (HSC) | CD34 |
| HSC, MSC | c-KIT |
| HSC, MSC progenitor | Colony forming unit (CFU) assay |
| Bone marrow | Bone marrow CFU |
| MSC | CD34+Sca-1+Lin |
| Mesenchymal | CD44 |

TABLE 1-continued

Cell specific markers.

| Cell Type | Marker Name |
| --- | --- |
| Erythroid | HLA-Dra |
| Cardiomyocytes | GATA4, ACTC, MLC-2v, Tnnt2 |
| Astrocyte | GFAP |
| Microglia | EMR1, CD44, iba-1 |
| Neuron | BM88, CAMK2a, GAD67, NSE, |
| Photoreceptor | Opsin |
| Beta cell | Insulin |
| ES Cells | Oct4, Nanog |

The third reporter nucleic acid sequence operably linked to a constitutive promoter, such as ubiquitin, is expressed while the cell is viable. The ubiquitin promoter is resistant to gene silencing by methylation, and is not regulated during the cell differentiation activity. Therefore, the signal associated with the expression of the reporter nucleic acid sequence linked to ubiquitin is "on" while the cells are alive and the said signal is "off" if the cells die at any point of time, regardless of the stages of differentiation, dedifferentiation, pluripotency, or cellular reprogramming.

One or more of the reporter nucleic acid sequences may encode a polypeptide, which is itself imagable or may be imagable upon reaction with a substrate or a probe or a target. The polypeptide may be imaged by optical imaging, MRI, PET, SPECT, or a combination thereof. PET has the advantage of being applicable to all living subjects. However, PET requires relatively short-lived radioactive tracers. The polypeptide may be bioluminescent or fluorescent. The bioluminescent or fluorescent polypeptide can be imaged by optical imaging. As used herein the term "bioluminescence polypeptide" or "bioluminescent protein" is a polypeptide or protein which produce bioluminescence on reaction with a substrate. Bioluminescence is relatively difficult to use for single cell imaging whereas fluorescence is highly sensitive for single cell imaging. The fluorescent reporter proteins are itself imagable, whereas the bioluminescent reporter proteins are imagable on reaction with a substrate. The PET imagable reporter protein can be imaged by using a probe or a target.

In one example, each of the first, second and third reporter nucleic acid sequence encodes a bioluminescent polypeptide, whereas in another example, each of the first, second and third reporter nucleic acid sequence may encodes a fluorescent polypeptide. The reporter nucleic acid sequence encoding bioluminescent polypeptide may be selected from a firefly luciferase (FL), a renilla luciferase (RL), or a gaussia luciferase (GL). Examples of the fluorescent polypeptides suitable for use in the present invention include, but not limited to, red fluorescence protein (RFP), and green fluorescence protein (GFP). The expression of a reporter nucleic acid sequence that encodes a fluorescent polypeptide can be measured by fluorescent-based cell sorting using fluorescent activated cell sorting (FACS). The each of the first, second or third reporter nucleic acid sequence may encode a protein, for example, Ferritin, which is an MR imagable protein. In some embodiments, the first, second or third reporter nucleic acid sequence encode HSV1-sr39 thymidine kinase, which is a PET imagable protein.

In one embodiment, the first reporter nucleic acid sequence encodes a bioluminescent protein, whereas the second reporter nucleic acid sequence encodes a fluorescent protein or vice versa. For example, the first reporter nucleic acid sequence may encode RL, wherein the second reporter nucleic acid sequence may encode GFP or vice versa. In other embodiment, both the first and second reporter nucleic acid sequences may encode bioluminescent protein, wherein the proteins are different and can be imaged independently at two different wavelengths. For one example, the first reporter nucleic acid sequence may encode RL, wherein the second reporter nucleic acid sequence may encode FL or vice versa. FL produces light in the 550-570 nm range, whereas RL produces a blue light at 480 nm. These enzymes can be used in dual-reporter assays due to their differences in substrate requirements and light output. In another embodiment, both the first and second reporter nucleic acid sequences may encode a fluorescent protein, wherein the proteins are different, and can be imaged independently at two different wavelengths. For one example, the first reporter nucleic acid sequence may encode GFP, wherein the second reporter nucleic acid sequence may encode RFP or vice versa.

In one aspect, the first reporter nucleic acid sequence may encode a PET reporter protein, such as Herpes Simplex virus type 1 thymidine kinase (HSV1-TK), wherein the second reporter nucleic acid sequence may encode a bioluminescence protein such as RL, or vice versa. In another aspect, the first reporter nucleic acid sequence may encode a PET reporter protein, such as HSV1-TK, wherein the second reporter nucleic acid sequence may encode a fluorescence protein, such as RFP or vice versa. In other aspect, the first reporter nucleic acid sequence may encode a PET reporter protein, such as HSV1-TK, wherein the second reporter nucleic acid sequence may encode an MRI imagable protein, such as Ferritin or vice versa. In yet another aspect, both the first and second reporter nucleic acid sequence may encode PET reporter protein, wherein the proteins are different and can be imaged at two different time points. In one embodiment, the first reporter nucleic acid sequence may encode a bioluminescent protein such as FL, wherein the second reporter nucleic acid sequence may encode a MRI imagable protein, such as Ferritin or vice versa. In other embodiment, the first reporter nucleic acid sequence may encode a fluorescent protein such as GFP, wherein the second reporter nucleic acid sequence may encode an MRI imagable protein, such as Ferritin or vice versa. In another embodiment, both the first and second reporter nucleic acid sequences may encode MRI imagable protein, wherein the two proteins are different by their different resonating signal.

The expression vector may further comprise a third reporter nucleic acid sequence, wherein each of the first, second and third reporter nucleic acid sequences may encode a bioluminescence protein or a fluorescent protein, wherein the three proteins are different and can be imaged at different wavelengths. For one example, the first reporter nucleic acid sequence may encode RL, the second reporter nucleic acid sequence may encode FL and the third reporter nucleic acid sequence may encode gaussia luciferase (GL). In one aspect, both the first and second reporter nucleic acid sequence may encode a bioluminescent protein, wherein the third reporter nucleic acid sequence may encode a PET imagable protein or vice versa. In other aspect, both the first and second reporter nucleic acid sequence may encode a bioluminescent protein, wherein the third reporter nucleic acid sequence may encode an MR imagable protein or vice versa. In another aspect, both the first and second reporter nucleic acid sequence may encode a fluorescent protein, wherein the third reporter nucleic acid sequence may encode a PET imagable protein or vice versa. In yet other aspect, both the first and second reporter nucleic acid sequence may encode a fluorescent protein, wherein the third reporter nucleic acid sequence may encode an MR imagable protein or vice versa. The first reporter nucleic acid sequence may encode a bioluminescent protein, the second reporter nucleic acid sequence may encode a fluorescent protein, wherein the third reporter nucleic acid sequence may encode a PET imagable protein or an MR imagable protein. In another aspect, the first reporter nucleic acid sequence may encode a fluorescent protein, the second reporter nucleic acid sequence may encode a bioluminescent protein, wherein the third reporter nucleic acid sequence may encode a PET imagable protein or an MR imagable protein.

The first reporter nucleic acid sequence may encode a PET imagable protein, the second reporter nucleic acid sequence may encode a fluorescent protein, wherein the third reporter nucleic acid sequence may encode an MR imagable protein. The first reporter nucleic acid sequence may encode a PET imagable protein, the second reporter nucleic acid sequence may encode an MR imagable protein, wherein the third reporter nucleic acid sequence may encode a fluorescent protein. In one aspect, first reporter nucleic acid sequence may encode an MR imagable protein, the second reporter nucleic acid sequence may encode a fluorescent protein, wherein the third reporter nucleic acid sequence may encode a PET imagable protein or a bioluminescent protein.

One or more embodiments of a method for monitoring a stem cell comprises delivering a first expression vector to the stem cell, wherein the first expression vector comprises a first reporter nucleic acid sequence and a second reporter nucleic acid sequence. The method further comprises monitoring of the stem cell by imaging at least one of the first or second reporter nucleic acid sequence expression. The first reporter nucleic acid sequence is operably linked to a first expression control sequence comprising a promoter for one or more pluripotency marker, for one example, Oct4 promoter. The second reporter nucleic acid sequence is operably linked to a second expression control sequence comprising a response element which is responsive to the binding of one or more response element specific protein, for one example, a GATA4 protein. The second expression control system further comprises a minimal promoter. The expression vector may further comprise a third reporter nucleic acid sequence operably linked to a third expression control sequence, wherein the third expression control sequence comprises a constitutive promoter, such as ubiquitin.

In some embodiments, the method comprise consecutive or simultaneous delivery of a first and a second expression vector to the stem cell, followed by monitoring the cells. The first expression vector comprises a first reporter nucleic acid sequence operably linked to a first expression control sequence comprising Oct4 promoter and a second reporter nucleic acid sequence operably linked to a second expression control sequence comprising a response element responsive to GATA4 binding. The second expression vector comprises a reporter nucleic acid sequence operably linked to an expression control sequence comprising a constitutive promoter, such as ubiquitin.

In some other embodiments, the method may comprise sequential or simultaneous delivery of a first, second, or a third expression vector to the stem cell, followed by monitoring the cell. The first expression vector may comprise a reporter nucleic acid sequence operably linked to an expression control sequence comprising Oct4. The second expression vector comprises a reporter nucleic acid sequence operably linked to an expression control sequence comprising a response element responsive to GATA4 binding and a minimal promoter operably linked to the response element. The third expression vector may comprise a reporter nucleic acid sequence operably linked to an expression control sequence comprising ubiquitin.

The expression vector may be delivered to the stem cell via transfection, transduction, nucleofection, or a combination thereof. The expression vector can be delivered by electroporation, which is approximately ten times as effective as chemical transfection. This procedure is also highly efficient for the introduction of foreign genes to cells, especially to mammalian cells. For example, electroporation may be used in the process of producing knockout mice, as well as in tumor treatment, gene therapy, and cell-based therapy.

In one embodiment, the expression vector may be delivered to the cells by transfection, where foreign DNAs are introduced into the eukaryotic cells. In one example, the expression vector may be delivered to a cell by nucleofection. Nucleofection provides the ability to transfect even non-dividing cells, such as neuron and resting blood cells. In other embodiment, the delivery of the expression vector can also be performed by DNA nanoparticle technique. The transfer of DNA nanoparticle can be monitored in real time fluorescence spectroscopy, by tracking the nanoparticle while the nanoparticle penetrates the cell and releases its DNA in the nucleus.

Useful delivery systems for stem cells of the invention may include the Sendai virus liposome delivery system, cationic liposomes, retrovirus expression vectors, adenovirus expression vectors, lentivirus expression vectors or a combination thereof. The use of liposomes as delivery vehicle is one particular method of interest. The liposomes may be fused with the cells of the target site to deliver their contents intracellularly.

Stem cells comprising the expression vector of the invention can be transplanted to various biological systems. The stem cell sample may be collected from the patient or donor animal, modified ex vivo by inserting expression vector of the present invention, and re-implanted into the patient or transplanted into another recipient. In one example, stem cells are collected from a patient, followed by expansion of the number of the cells in culture, and then induced to differentiate as specific cells, such as cardiac cells. At any time during the method, the expression vector comprising reporter nucleic acid sequence may be introduced into the cells. The stem cells may be transplanted into the patient or implanted into one or more different recipient(s) of the same or different species. Then the cells can be monitored to determine different cellular stages for stem cells.

The delivery of expression vector or vectors to cell may be observed by monitoring the expression of the reporter protein. The cell may be a stem cell, wherein the stem cell is selected from a unipotent stem cell, a pluripotent stem cell, a multipotent stem cell, a totipotent stem cell, or an induced pluripotent stem cell. In some embodiments, cultured cells or a progeny of the cultured cells may comprise the expression vector comprising two or more reporter nucleic acid sequences.

The method for monitoring differentiation status of the stem cell is performed in vivo. The differentiation status of the stem cell may be monitored in various tissues, which include but not limited to, a muscle tissue, a connective tissue, a neural tissue, a cardiac tissue, or an adipose tissue. The monitoring of stem cell may identify the presence, absence, concentration, localization, or differentiation status of the stem cell. Depending on intensity of light produced by luminescent or fluorescent reporter proteins, the concentration of stem cells may be determined. By monitoring and tracking the imaged cells, localization of stem cells at a particular point of time, in a specific tissue or organ may be determined. Depending on color change of different reporter proteins, the stages of differentiation or pluripotency may be identified.

The stem cells transfected with the expression vector comprising the first, second and third reporter nucleic acid sequence. The first reporter nucleic acid sequence operably linked to the Oct4 promoter, which is a cell specific promoter activated only when the cell is a stem cell. Therefore, the first reporter nucleic acid encoding reporter protein expressed while the cells are pluripotent stem cells. However, the reporter protein is not expressed while the stem cells are in differentiation state. The second reporter nucleic acid sequence operably linked to the response element for GATA4 protein binding. GATA4 protein is a cell specific protein activated only when the cell is a cardiac cell. Therefore, the second reporter nucleic acid encoding reporter protein expressed while the cells are cardiac cells. However, the reporter protein is not expressed while the cardiac cells are de-differentiated into stem cells.

An embodiment of the kit of the invention for monitoring stem cells comprises an expression vector. The expression vector may comprise a first reporter nucleic acid sequence operably linked to a first expression control sequence; and a second reporter nucleic acid sequence operably linked to a second expression control sequence. The first expression control sequence comprises an Oct4 promoter, and the second expression control sequence comprises a response element that is responsive to GATA4 protein binding and a minimal promoter.

The kit may further comprise an additional expression vector, wherein the additional expression vector may comprise a reporter nucleic acid sequence operably linked to an expression control sequence comprising a constitutive promoter, such as ubiquitin. The kit may also comprise cells (e.g., in a frozen condition) and/or medium for culturing cells. The kit may further comprise a protocol for handling expression vector(s) and/or cells, delivering expression vectors to the cells or culturing of the cells. The kit may be packaged along with a manual describing the method of using the kit. In a specific embodiment, the kit may comprise a stem cell or a progeny of stem cell comprising an expression vector wherein the expression vector may comprise a first reporter nucleic acid sequence operably linked to an Oct4 promoter; and a second reporter nucleic acid sequence operably linked to a response element for binding GATA4 protein and a minimal promoter.

For using ES cells as a source for therapeutic application, challenges are immune rejection and tumorogenicity of implanted ES cells. Such problems associated with immune rejection of implanted ES cells may be eliminated by using patient specific pluripotent stem cells generated by reprogramming of somatic cells collected from the said patient. The in vitro and in vivo assessment of pluripotency of ES cell may be helpful in the detection of tumorogenicity and in developing a strategy for preventing tumorogenicity.

Example 1

Culture of Undifferentiated Embryonic Stem Cells Using Serum Free Medium

Murine ES-D3 cell line (CRL-1934) was obtained from the American Type Culture Collection (ATCC; Manassas, Va.). ES cells were maintained in an undifferentiated, pluripotent state by incubating with 1000 IU/mL leukemia inhibitory factor at 37° C. (LIF; Chemicon, ESGRO, ESG1107) in a humidified incubator with 5% $CO_2$ in air. ES cells were cultured on 0.1% gelatin-coated plastic dishes using ES culture medium wherein the culture medium was Knockout Dulbecco modified Eagle medium. The Eagle medium was supplemented with 15% Knockout serum replacement, 0.1 mmol/L of β-mercaptoethanol, and 2 mmol/L of glutamine. The ES culture medium was changed every day, and ES cells were passaged every 2 to 3 days.

Example 2

In Vitro Differentiation of Embryonic Stem Cells

In vitro differentiation of ES cells was performed by withdrawal of LIF and addition of high concentration of fetal bovine serum. ES cells were cultured on 0.1% gelatin coated plastic dishes in differentiation medium containing Iscove's Dulbecco modified Eagle medium supplemented with 15% fetal bovine serum, 0.5 mmol/L monothioglycerol, and 2 mmol/L glutamax. The culture medium for ES was changed every day after optical imaging of cells with coelentrazine or D-luciferin.

Example 3

Construction of Stem Cell Specific and Constitutive Promoter Driven Optical Reporter Gene Systems A gene fragment of stem cell specific Oct4 promoter was released from plasmids by restriction digestion with HindIII and NotI restriction enzymes. NotI restriction enzyme site was produced in the CMV promoter region of pRL-CMV vector (Promega) and then digested with HindIII and NotI restriction enzymes. Sticky-end fragment of Oct4 promoter was ligated into pRL-CMV vector in an upstream region of the renilla luciferase gene to make Oct4 promoter driven renilla luciferase construct (Oct4-hRLuc). A gene fragment of Oct4 promoter was released from Oct4-hRLuc with HindIII and BglII restriction enzymes and ligated into multiple cloning site pGL4.10 vector (Promega) to make Oct4 promoter driven humanized firefly luciferase construct (Oct4-FLuc2). To make ES cells with Oct4-hRLuc, Oct4 promoter driven hRLuc segment was released from Oct4-hRLuc with BglII and XbaI restriction enzymes and ligated into pcDNA 3.1 puro that had digested with the same restriction enzymes (puro Oct4-hRLuc). Lentiviral vector comprising fusion protein of ubiquitin promoter driven firefly luciferase-enhanced green fluorescence protein (Ubiq-FLuc-eGFP) was made.

Figure 1:
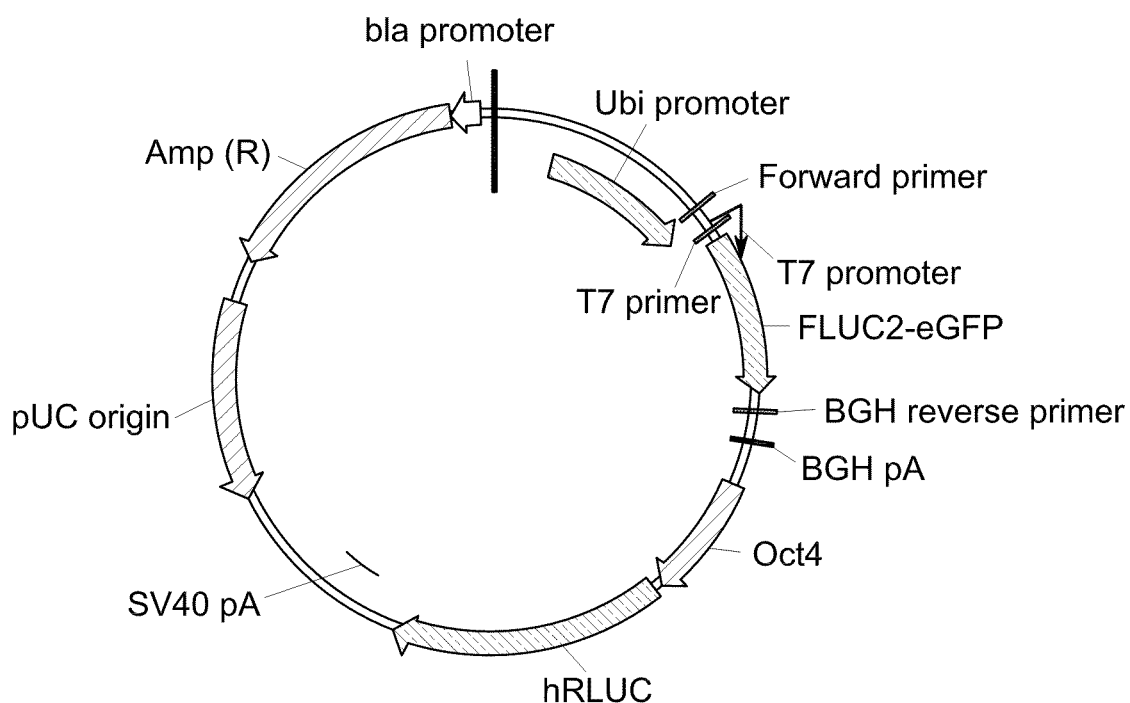

To generate a bi-functional reporter gene system that encodes firefly luciferase (FLuc) fused to eGFP, FLuc-eGFP (FG) was PCR amplified from a triple fusion reporter gene construct containing FLuc-eGFP and truncated Herpes Simplex Thymidine Kinase. The following primers were used to generate a stop condon for eGFP and the cloning sites BamHI and KpnI at the 5' end and the 3' end respectively: 5'-gcggatccGCCACCATGGAAGACGCCAA-3' (SEQ ID NO: 1) and 5'-gcggtaccctaCTTGTACAGCTCGTCCAT-GCCG-3' (SEQ ID NO: 2). This fragment was then cloned into pHRG (promoter less reporter plasmid containing renilla luciferase gene) to create pHRFG. Ubiquitin promoter was PCR amplified from pFUG using the following primers to generate a Cla1 site at the 5' end: 5'-ggggatcga-tAACCCGTGTCGGCTCCAGAT-3' (SEQ ID NO: 3) and 5'-GGCGTCTTCCATGGATCCTC-3' (SEQ ID NO: 4). This fragment was then ligated into the Cla1 and BamH1 sties of pHRFG to create pHRUFG. Finally, a vector (FIG. 1) containing two expression control sequences for two different genes Oct4-hRLuc and Ubiq-FLuc-eGFP was made. FIG. 1 shows of a construct of the invention with constitutive Ubiquitin promoter, and a cell specific Oct4 promoter.

Example 4

Transient Transfection and Assessment of Stem Cell Specificity of Oct4-hRLuc and Oct4-FLuc2 with Firefly, and Renilla Luciferase Assays Mouse ES cells, rat myoblast (H9C2) cells, and human kidney cancer cells (HEK-293T) were transiently transfected with Oct4-hRLuc and Poct4-Fluc2 with liposome based method. 200 ng/well of DNA and Lipofectamine™ 2000 were used for the transfection. Unless otherwise specified, 5 ng/well of other optical reporters such as CMV promoter driven FLuc2 (CMV-FLuc2) or CMV promoter driven hRLuc (CMV-hRLuc)) were used for transfection normalization in all the transient transfection studies. Mouse ES cell, H9C2 and HEK-293T were transiently transfected with CMV-hRLuc and CMV-Fluc2 as control. Firefly, and renilla luciferase assays were performed at 48 hours after the transient transfection. The luminometer assays for firefly luciferase and renilla luciferase activity were performed as described below. In brief, transfected cells were lysed in 200 ml of ice-cold 1× passive lysis buffer supplied by Promega and were shaken for 15 min on ice. The cell lysate was centrifuged for 5 min at $1.3 \times 10^4$ g at 4° C. to remove cell debris. To determine renilla luciferase activity, 20 ml of supernatant was assayed by addition of 0.5 mg of coelenterazine in 100 ml of phosphate buffered saline at pH 7.0 (PBS), followed by photon counting in the luminometer (model T 20/20; Turner Designs, Sunnyvale, Calif.) for 10 sec. Firefly luciferase activity was determined as described for renilla luciferase activity, except 100 ml of luciferase assay reagent II (LARII) substrate from Promega was used instead of coelenterazine. Protein concentration in cell lysate was determined by Bradford assay reagent (Bio-Rad Laboratories, Hercules, Calif.). Renilla luciferase activity was normalized for protein content and for transfection efficiency using firefly luciferase activity and expressed as relative light units (RLU) per microgram protein per minute of counting. Firefly luciferase activity was normalized for protein content and for transfection efficiency using renilla luciferase activity as well.

Figure 2B:
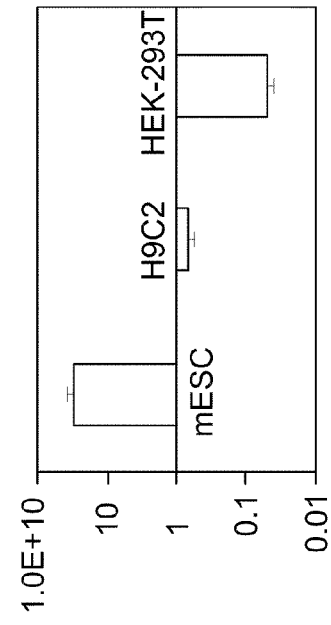
Figure 2D:
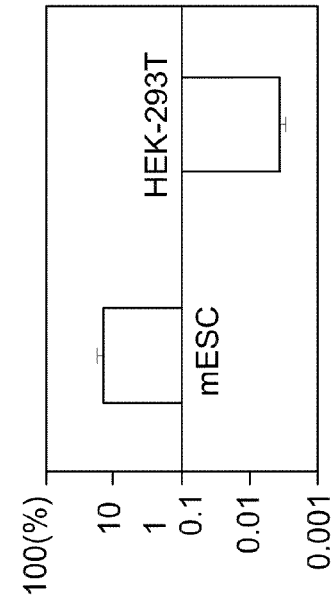
Figure 2A:
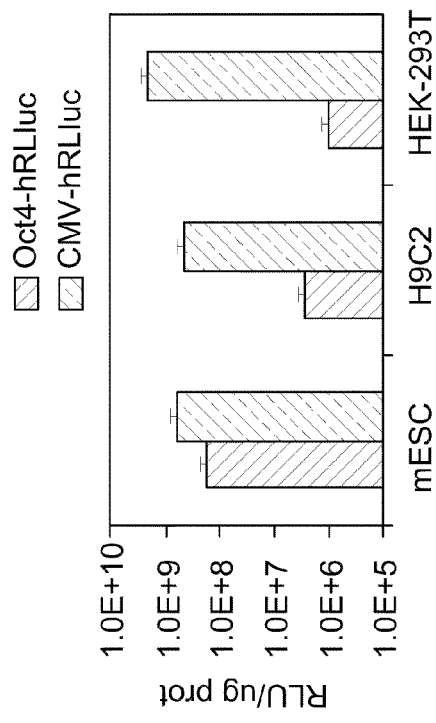
Figure 2C:
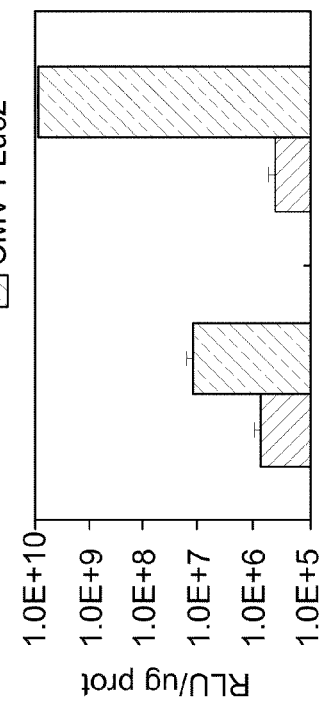

With Oct4-hRLuc and CMV-hRLuc transfection, mouse ES cells showed higher Oct4 promoter activity, but similar or lower CMV promoter activity than H9C2 and HEK-293T cells. Oct4 promoter activity (normalized by CMV promoter activity) was 43 and 647 fold higher in mouse ES cells compared to H9C2 and HEK-293 cells respectively (T-test, p=0.002). With Oct4-FLuc2 and CMV-FLuc2 transfection, mouse ES cells showed higher Oct4 promoter activity, but lower CMV promoter activity than that of HEK-293T cells. Oct4 promoter activity normalized by CMV promoter activity was 401 folds higher in mouse ES cells compared to HEK-293 cells respectively (T-test, p=0.001). FIGS. 2A to 2D are graphs representing the specificity of Oct4 expression for embryonic stem cell compared to differentiated adult cell lines. FIG. 2A showed higher Oct4-hRLuc activity for mouse ES cells compared to those of H9C2 and HEK-293T cells, but similar or lower CMV promoter activity than those of H9C2 and HEK-293T cells. FIG. 2B showed Oct4-hRLuc activity normalized by CMV-hRLuc activity, where Oct4-hRLuc activity was significantly higher than those of H9C2 and HEK-293 cells. FIG. 2C showed higher Oct4-FLuc2 activity for mouse ES cells compared to that of HEK-293T cells, but lower CMV promoter activity than that of HEK-293T cells. FIG. 2D showed Oct4-FLuc2 activity normalized by CMV-FLuc2 activity where Oct4-FLuc2 activity was significantly higher than that of HEK-293 cells.

Example 5

Transient ES Cell Transfection and Change of Oct4-hRLuc Activity Over Time

Mouse ES cells were transiently transfected with Oct4-hRLuc and CMV-FLuc2 using liposome based method and cultured in differentiation medium. Firefly and renilla luciferase assays were performed for the period of 1 to 6 days after the transfection using luminometer assay. To assess Oct4 promoter activity per cell, Oct4-hRLuc activity was normalized by CMV-FLuc2 activity.

Figure 3:
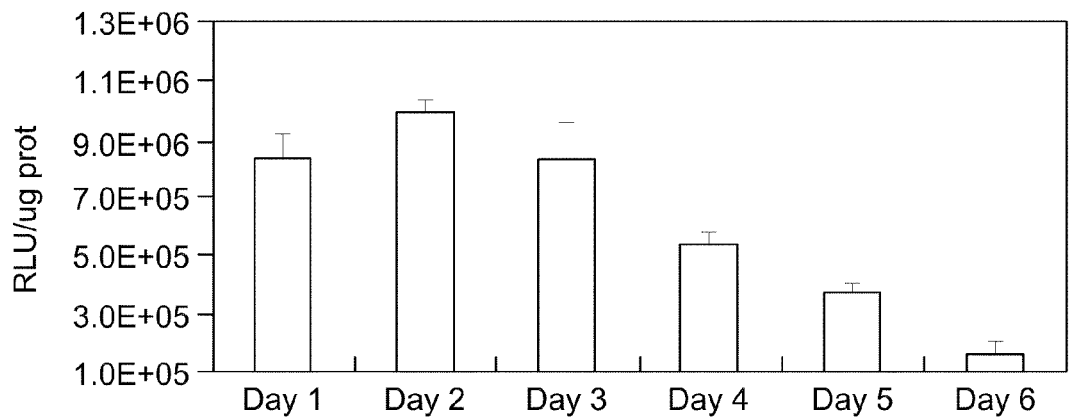

Oct4 promoter activity normalized by CMV promoter activity in mouse ES cells was measured. Mouse ES cells were transient-transfected using liposome with Oct4-hRLuc and CMV-FLuc2. Oct4 activity was highest in 2 days after the transfection and then the activity is gradually decreased over 4 days. FIG. 3 illustrates that the transfected mouse ES cell showed highest normalized RLuc activity at 2 days transfection and thereafter normalized RLuc activity gradually decline over time.

Example 6

Making of Stable ES Cells with Oct4-hRLuc and Ubiq-Fluc-eGFP

Mouse ES cells were transfected with puro Oct4-hRLuc and Ubiq-Fluc-eGFP by liposome-based transfection and selected with puromycin (concentration of 500 ng/ml). After getting mouse ES cells stably expressing Oct4-hRLuc, the cells were resuspended in OptiMEM with 8 μg/ml Polybrene (Sigma). Cells were transduced at a multiplicity of infection of 5 for 3 hrs in a cell culture incubator at 37° C. and 5% $CO_2$. After 3 hrs fresh growth media was added to the cells. Cells were then incubated for 48-72 hrs before sorting and analyzing by flow cytometry and bioluminescence imaging. Transfection efficiency of the virus was 71% and cells with highest eGFP expression were sorted for further experiment.

Example 7

Change of Oct4-hRLuc and Ubiq-FLuc-eGFP Activities in Cultured Cell Using Differentiation Medium Mouse ES cells stably expressing both Oct4-hRLuc and Ubiq-FLuc-eGFP were plated on 6 well plates ($10^5$/well) with serum free ES cell maintenance medium. After 24 hours, cells were transferred to differentiation medium. Renilla luciferase and firefly luciferase activities were determined by bioluminescence imaging using a cooled charge coupled device (CCD) camera (Xenogen IVIS; Xenogen Corp. Alameda, Calif.) using D-luciferin and coelenterazine.

Figure 4A:
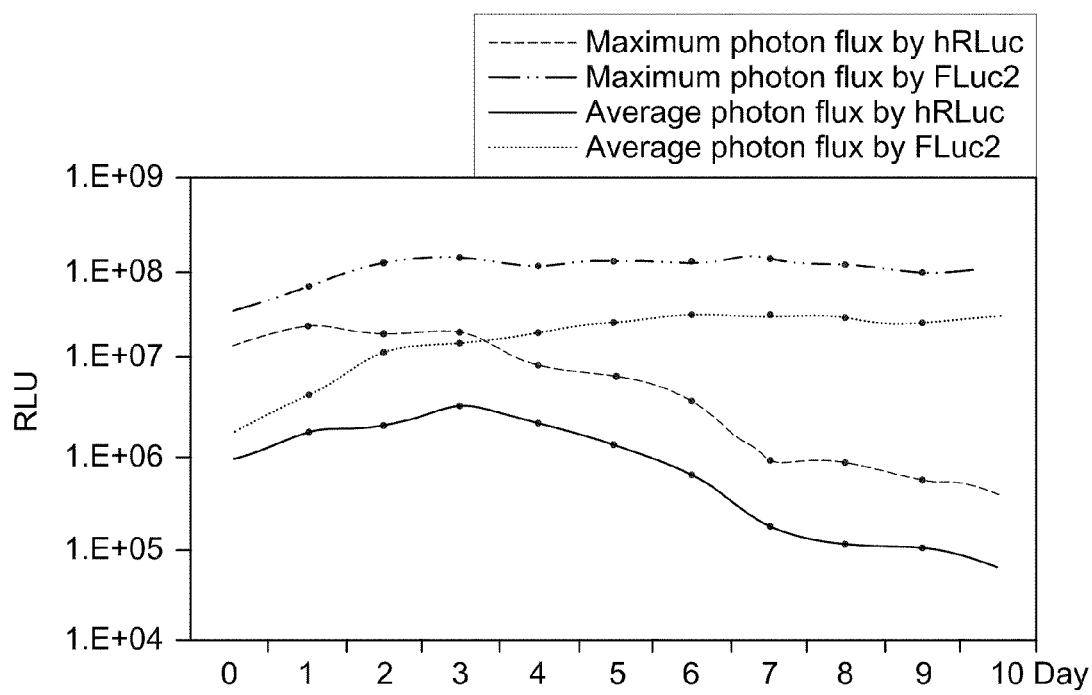
Figure 4B:
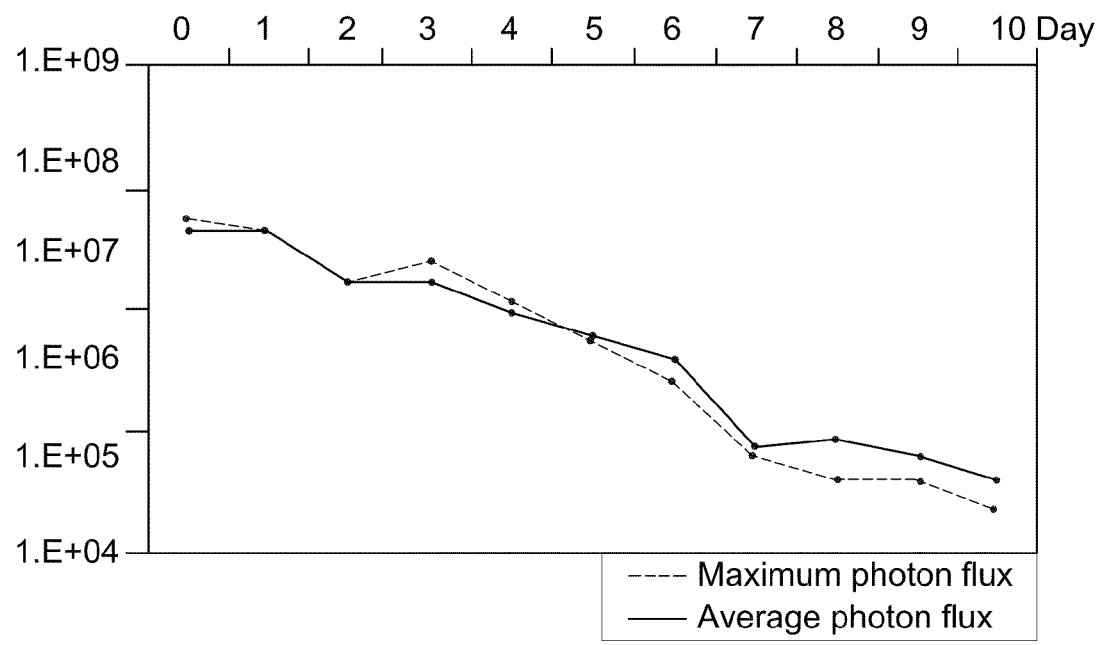
Figure 5:
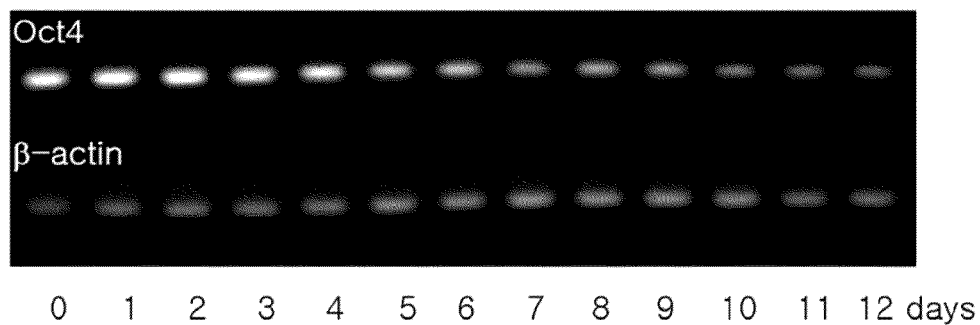
FIG. 5 is an agarose gel photograph of PCR amplified product of Oct4 mRNA level and β-actin mRNA level over time.

Activity of hRLuc and Fluc2 of mouse ES cells stably expressing Oct4-hRLuc and Ubiq-FLuc-eGFP in cell culture using the differentiation medium over time. Ubiq-FLuc activity is increased with increasing number of cells whereas Oct4-hRLuc activity is decreased (FIG. 4A) in differentiation medium in spite of increasing the number of cells. Oct4-hRLuc activity is normalized by Ubiq-Fluc activity wherein both the activities are decreasing over time (FIG. 4B). FIGS. 4A-B are graphs illustrating luciferase activity of mouse ES cells that stably expresses Oct4-hRLuc and Ubiq-FLuc-eGFP in differentiation medium over time. PCR analysis showed decrease of Oct4 mRNA level over time. FIG. 5 represents PCR amplified mRNA level of Oct4 that decrease over time.

Example 8

Changes of Oct4-hRLuc and Ubiq-FLuc-eGFP Activity of Mouse ES Cells Xenograft in Living Mice Animal handling was performed in accordance with Stanford University Animal Research Committee guidelines. Mice were gas anesthetized using isofluorane (2% isoflurane in 100% oxygen, 1 L/min) during all injection and imaging procedures. Mice were imaged using a cooled charge-coupled device (CCD) camera (Xenogen IVIS29; Xenogen Corp.). Mouse ES cells ($1 \times 10^6$) were stably cotransfected with Oct4-hRLuc and Ubiq-FLuc-eGFP. Then the cells were implanted to a female mouse of 7 weeks old (nu/nu, Charles River). To determine the Oct4 promoter activity in the implanted ES cells in living mouse, 20 μg of coelenterazine in a mixture of 5% ethanol and 95% PBS (final volume 200 μL) was injected via tail vein, and the mouse was immediately imaged with the IVUS system with an acquisition time of 1 min. The animals were placed in a light-tight chamber, and a gray scale reference image was obtained under low-level illumination. Images were obtained using Living Image Software (Xenogen Corp.) and Igor Image Analysis Software (Wavemetrics) after collecting photons emitted from the implanted cells. To quantify the measured light, the average and maximum photons per second per square centimeter per steradian were determined over regions of implanted cells.

To determine Ubiqutin promoter activity in the implanted ES cells in living mouse, 3 mg of D-Luciferin in PBS (final volume, 200 μL) was injected via tail vein and the mouse was imaged after 5 min with the IVUS system with an acquisition time of 1 min until light output reaches at maximal point. Data analyses were same as coelenterazine imaging as described above.

Figure 6B:
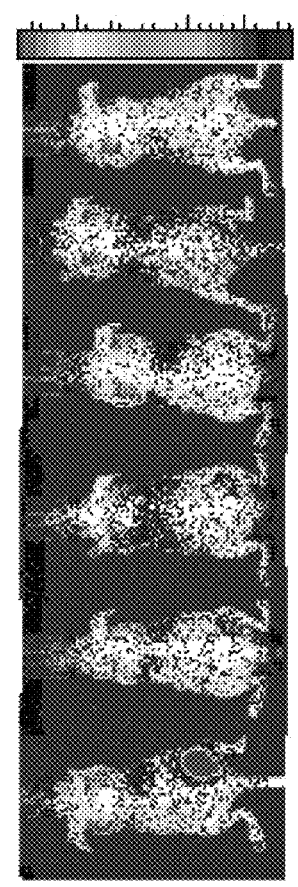
FIG. 6A is a graph and a FIG. 6B is an image of mice in a series, showing luciferase expression in ES cells comprising Oct4-hRLuC expression vector in live mice.
FIG. 6C is a graph and a FIG. 6D is an image of mice in a series, showing luciferase expression in ES cells comprising Ubiq-Fluc expression vector in live mice.
Figure 6D:
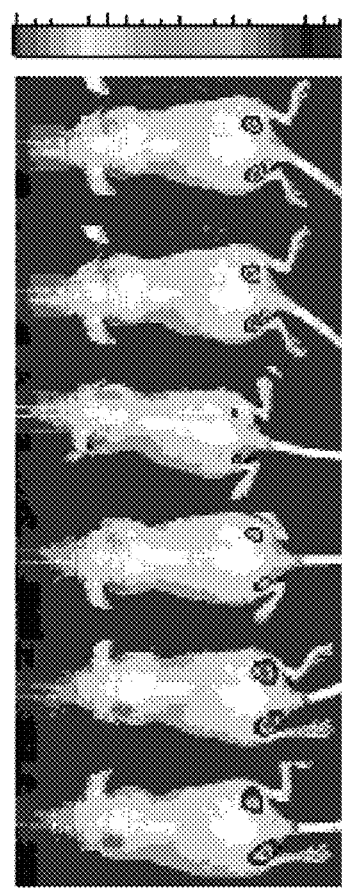
Figure 6A:
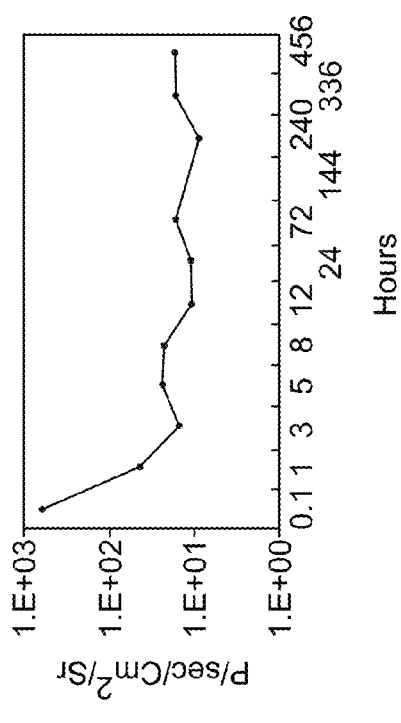
Figure 6C:
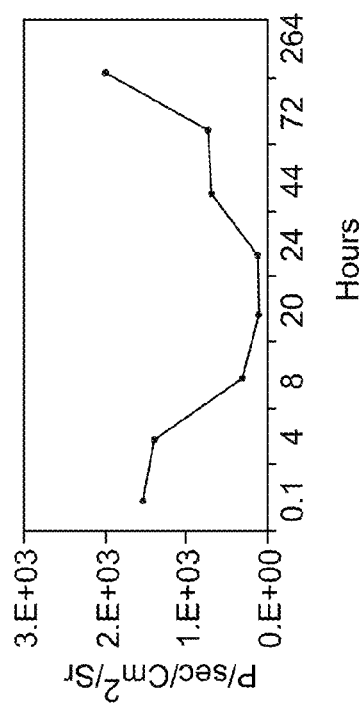

Mouse ES cells stably expressing Oct4-hRLuc and Ubiq-FLuc-eGFP were monitored to determine luciferase activity. Activity of Oct4-hRLuc of xenograft decreased rapidly. The image was taken after 24 hours while the activity of Oct4-hRLuc was about 1.7% of the activity measured at 5 min after implantation of mouse ES cells. Ubiq-FLuc activity was also decreased and became 19% of initial activity while the image was acquired at 24 hour after implantation but thereafter the activity was gradually increased. FIG. 6A-D represent change of Oct4-hRLuc and Ubiq-FLuc-eGFP activity of xenograft in living mice. FIGS. 6A and 6B illustrate Oct4-hRLuc activity of xenograft decreased rapidly and after 24 hrs, it became 1.7% of the activity measured at 5 min after implantation of the cell. FIGS. 6C and 6D illustrate Ubiq-FLuc activity decreased gradually and after 24 hrs, it became 19% of the activity measured at 5 min after implantation of the cell, but thereafter it gradually increased. FIGS. 6 A-B show images of cell differentiation status by imaging Oct4-hRLuc activity of xenograft that shows rapid decrease of signal within 24 hour after the implantation. FIG. 6C shows a graph and FIG. 6D show a series of images of mice after implantation by imaging Ubiq-FLuc activity that shows initial decrease followed by gradual increase after 72 hours to track the cell survival.

Example 9

Creation of GATA-4 Responsive Element Reporter Gene (GRERG) System

Figure 7:
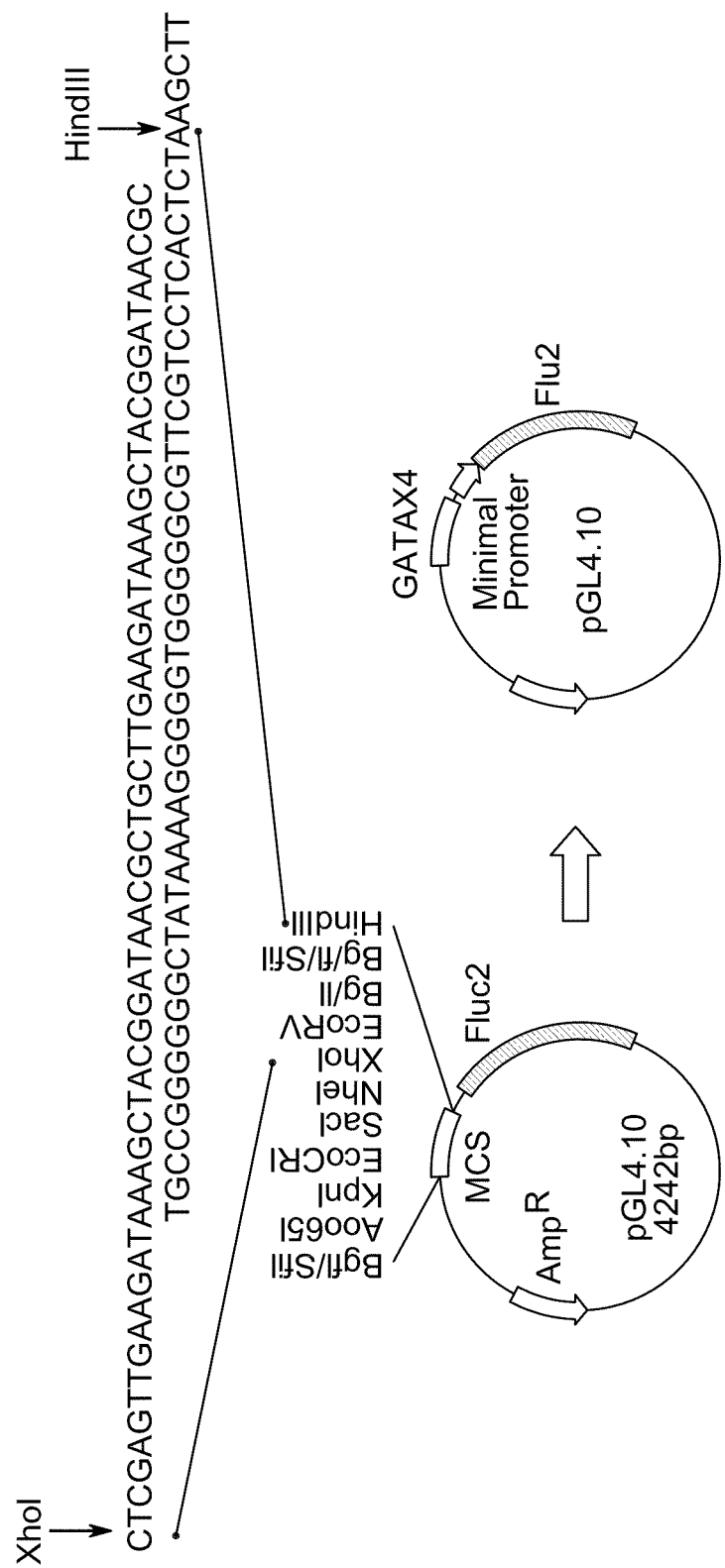
FIG. 7 is a schematic drawing of an example of the method of the invention for making an expression vector by inserting a response element that is responsive to the binding of a GATA4 protein, and a minimal promoter sequence into the multiple cloning site.

Transcriptional factor responsive reporter gene imaging technique was developed to determine expression of GATA4 binding protein that is crucial for endoderm and cardiac differentiation. GATA4 binding protein responsive element reporter gene system (GRERG) was constructed by linking 4 copies of GATA binding sequences with minimal promoter (from PG5luc vector) driving humanized firefly luciferase gene. PGL4.10 (from Promega) was used as a backbone. Four GATA binding sequence and major late promoter sequence of adenovirus was sequentially inserted into the multiple cloning site of pGL4.10. XhoI and HindIII restriction enzyme sites were used to insert GATA responsive element (FIG. 7). Four GATA binding sequence and a major late promoter sequence of adenovirus were sequentially inserted into multiple cloning site of pGL4.10, as showed in FIG. 7.

Example 10

Making Vector that Produce GATA4 Binding Protein

Figure 8:
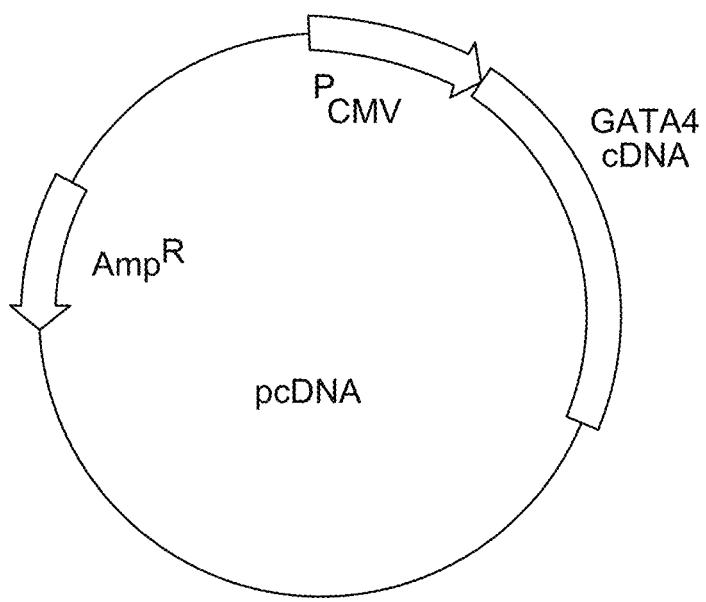
FIG. 8 is a schematic drawing of an embodiment of an expression vector of the invention comprising cDNA-encoding GATA4 protein in pcDNA vector backbone.
Figure 9:
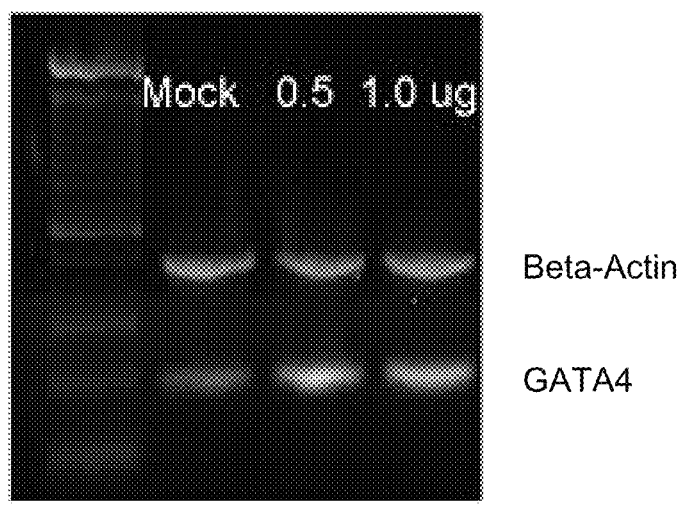
FIG. 9 is an agarose gel photograph of PCR amplified product of the cDNA sequence that encodes GATA4 protein.

Plasmid with cDNA for GATA4 binding protein was purchased from Openbiosystem. The cDNA sequence was amplified with PCR. Restriction enzyme sites of NheI and XhoI were introduced at each end of the PCR amplified DNA. The gene of interest was cloned into mammalian cell expressing pcDNA 3.1 vector (FIG. 8). The vector was transfected into HEK 293 cell and expression of GATA4 binding protein was evaluated. Cells transfected with the vector showed higher expression of GATA4 binding protein mRNA (FIG. 9). FIG. 9 is an image of PCR amplification of the cDNA sequence that encodes GATA4 protein.

Example 11

Reporter Gene Expression: Luminometer Assay (In Vitro) and Bioluminescence Imaging (In Vivo)

Figure 10:
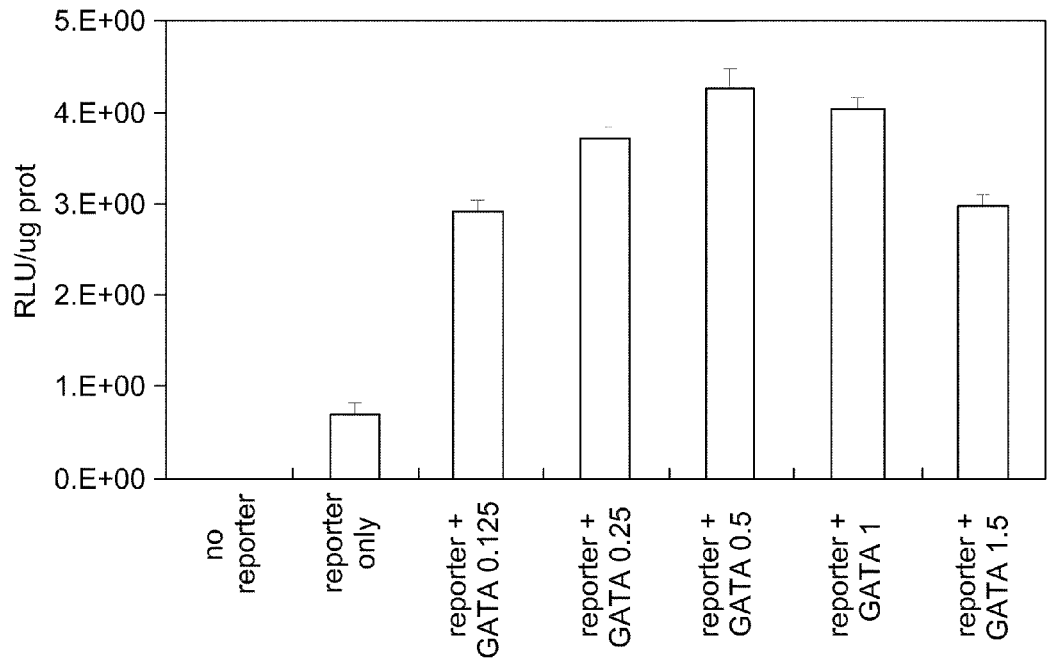
FIG. 10 is a bar graph of luciferase expression of a reporter nucleic acid sequence operably linked to a response element responsive to the binding of a GATA4 protein, in vitro.

The constructed expression vectors were contransfected into HEK 293 cells to determine the expression of GATA4 binding protein responsive element driven reporter gene system (GRERG). Transfection was performed using Lipofectamine™ 2000 (Invitrogen). Several different concentration of GATA4 binding protein expression vector was applied to optimize appropriate vector dose. Luciferase activity of GRERG was measured by luminometer assay where activity of GRERG increased by co-transfection of GATA4 binding protein expression vector as shown in FIG. 10. The luciferase activity measured (Luminometer) from HEK 293T cells transfected with fixed concentration of GRE-luciferase and co-transfected with increasing concentration of plasmid vector expressing GATA binding protein. Increasing expression of GATA4 protein activates the expression of luciferase by binding with the GATA4-response element.

The rate of increase of GRERG-activity is (about 6 fold) proportional to the concentration of GATA4 binding protein expression vector. Luciferase activity for GRERG was measured by bioluminescence imaging (BLI) assay (using IVUS) in HEK 293 cells. The BLI activity of GRERG was also increased by co-transfection of GATA4 binding protein expression vector in HEK 293 cells (FIG. 11). The activity of GRERG was increased by about 6 fold while cotransfecting cells with 1 µg GATA4 binding protein expression vector compared to GRERG alone (without GATA4 binding protein expression vector). FIG. 11 is a bar graph of luciferase activity measured (CCD camera imaging) from HEK 293T cells transfected with fixed concentration of GRE-luciferase, and co-transfected with increasing concentration of plasmid vector expressing GATA binding protein. Increasing expression of GATA4 protein activates the expression of luciferase by binding with the GATA4-response element.

The constructed expression vectors were cotransfected into HCT 116 cells to determine expression of GATA4 binding protein responsive element reporter gene (GRERG) system. The transfection was performed by Lipofectamine™ 2000 (Invitrogen). GATA4 binding protein expression vector was applied in several different concentration for optimization of vector dose. Luciferase activity of GRERG measured by BLI (using IVUS) assay was also increased by co-transfection of GATA4 binding protein expression vector in HCT 116 colon cancer cells. The activity of GRERG was increased by about 16 fold while cotransfecting cells with 1.5 µg of GATA4 binding protein expression vector compared to GRERG alone (without GATA4 binding protein expression vector) as shown in FIG. 12. Luciferase expression measured (FIG. 12) from HCT 116 colon cancer cells transfected with a fixed concentration of GRE-Fluc reporter, and co-transfected with different doses of GATA4 binding protein by bioluminescence imaging. Luciferase activity of GRERG measured by BLI (using IVUS) assay was also increased by treatment with 5 azacytidine in HCT 116 colon cancer cells as shown in FIG. 13. Luciferase expression increases with time (1 to 3 hrs) in HCT 116 colon cancer cells transfected with GRE-FLUC, after treating with 5-azacytidine. The 5-azacytidine normally activates endogenous GATA expression.

Example 12

Construction of Stem Cell Specific, Constitutive and Inducible Promoter Driven Optical Reporter Gene Systems A gene fragment of stem cell specific Oct4 promoter was released from plasmids by restriction digestion with HindIII and NotI restriction enzymes. Sticky-end fragment of Oct4 promoter was ligated into pRL-CMV vector in an upstream region of the renilla luciferase gene to make Oct4 promoter driven renilla luciferase construct (Oct4-hRLuc). To make ES cells with Oct4-hRLuc, Oct4 promoter driven hRLuc segment was released from Oct4-hRLuc with BglII and XbaI restriction enzymes and ligated into pcDNA 3.1 puro that had digested with the same restriction enzymes (puro Oct4-hRLuc).

A bi-functional reporter gene system that encodes firefly luciferase (FLuc) fused to eGFP, FLuc-eGFP (FG) was PCR amplified from a triple fusion reporter gene construct containing FLuc-eGFP and truncated Herpes Simplex Thymidine Kinase. This fragment was then cloned into pHRG (promoter less reporter plasmid containing renilla luciferase gene) to create pHRFG. Ubiquitin promoter was PCR amplified from pFUG using the following primers to generate a ClaI site at the 5' end: 5'-ggggatcgatAACCCGTGTCG- GCTCCAGAT-3' (SEQ ID NO: 3) and 5'-GGCGTCTTC-CATGGATCCTC-3' (SEQ ID NO: 4). This fragment was then ligated into the Cla1 and BamH1 sties of pHRFG to create pHRUFG. Expression control sequence for ubiquitin was further cloned in pcDNA 3.1 containing Oct4-hRLuc to form a construct having Oct4-hRLuc and Ubiq-FLuc-eGFP. The cDNA sequence for GATA4 binding protein was amplified with PCR. Restriction enzyme sites of NheI and XhoI were introduced at each end of the PCR amplified DNA. The gene of interest was cloned into mammalian cell expressing pcDNA 3.1 vector. Finally the GRERG sequence was introduced in pcDNA 3.1 containing Oct4-hRLuc and Oct4-hRLuc and Ubiq-FLuc-eGFP to form a vector with three expression control sequences (FIG. 14).

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A plasmid expression vector for monitoring differentiation status of stem cells, comprising:
   a first reporter nucleic acid sequence encoding a human renilla luciferase (hRLUC) polypeptide operably linked to an Oct4 promoter;
   a second reporter nucleic acid sequence encoding a polypeptide selected from a green fluorescence protein (GFP), a red fluorescence protein (RFP), or a thymidine kinase (TK) operably linked to a second expression control sequence comprising a minimal promoter and a response element, wherein the response element comprises at least four repeats of GATA-4 protein-binding sequence, and wherein the response element is responsive to binding of at least one response element specific protein GATA4; and
   a third reporter nucleic acid sequence encoding a double fusion polypeptide of a firefly luciferase and a green fluorescence protein (FLUC2-eGFP) operably linked to an ubiquitin promoter.

2. The plasmid expression vector for monitoring differentiation status of stem cells of claim 1, wherein the minimal promoter is selected from the group consisting of CMV promoters, adenovirus early promoters, adenovirus late promoters, and TATA Box promoters.

3. A cultured cell comprising the plasmid expression vector for monitoring differentiation status of stem cells of claim 1.

4. A kit for monitoring stem cells, comprising:
   a plasmid expression vector for monitoring differentiation status of stem cells, comprising:
      a first reporter nucleic acid sequence encoding a human renilla luciferase (hRLUC) polypeptide operably linked to an Oct4 promoter;
      a second reporter nucleic acid sequence encoding a polypeptide selected from a green fluorescence protein (GFP), a red fluorescence protein (RFP), or a thymidine kinase (TK) operably linked to a second expression control sequence comprising a minimal promoter and a response element, wherein the response element comprises at least four repeats of GATA-4 protein-binding sequence, and wherein the response element is responsive to binding of at least one response element specific protein GATA4; and
      a third reporter nucleic acid sequence encoding a double fusion polypeptide of a firefly luciferase and a green fluorescence protein (FLUC2-eGFP) operably linked to an ubiquitin promoter.

* * * * *